US00PP27986P2

(12) United States Plant Patent
Hoogenraad

(10) Patent No.: US PP27,986 P2
(45) Date of Patent: May 9, 2017

(54) ***PHYSOCARPUS* PLANT NAMED 'HOOGI021'**

(50) Latin Name: *Physocarpus opulifolius*
Varietal Denomination: Hoogi021

(71) Applicant: Mark Sebastiaan Hoogenraad, Ederveen (NL)

(72) Inventor: Mark Sebastiaan Hoogenraad, Ederveen (NL)

( * ) Notice: Subject to any disclaimer, the term of this patent is extended or adjusted under 35 U.S.C. 154(b) by 57 days.

(21) Appl. No.: 14/756,840

(22) Filed: Oct. 21, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — June Hwu
(74) *Attorney, Agent, or Firm* — Penny J. Aguirre

(57) ABSTRACT

A new cultivar of *Physocarpus opulifolius* plant named, 'Hoogi021', that is characterized by its dwarf and compact plant habit; reaching 40 cm in height as a four year-old plant in the landscape, its very small size leaves that emerge brown-purple and mature to green suffused with black, and its small white-pink flowers in spring.

2 Drawing Sheets

Botanical classification: *Physocarpus opulifolius.*
Varietal denomination: 'Hoogi021'.

BACKGROUND OF THE INVENTION

The present invention relates to a new and distinct cultivar of *Physocarpus opulifolius* and will be referred to hereafter by its cultivar name, 'Hoogi021'. 'Hoogi021' represents a new cultivar of *Physocarpus*, a deciduous shrub grown for landscape use.

The new *Physocarpus* arose from a breeding program conducted by the Inventor in Ederveen, The Netherlands. The objective of the breeding program was to develop new *Physocarpus* cultivars with a compact plant habit.

The new *Physocarpus* originated from seed collected in 2008 and sown in 2009 from an open pollinated plant of *Physocarpus opulifolius* 'Monlo' (U.S. Plant Pat. No. 11,211). 'Hoogi018' was selected as a single unique plant from amongst 350 seedlings evaluated in 2012.

Asexual propagation of the new cultivar was first accomplished by stem cuttings by the Inventor in 2012 in Ederveen, The Netherlands. Asexual propagation by stem cuttings has determined that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Hoogi021' as a unique and distinct cultivar of *Physocarpus.*

1. 'Hoogi021' exhibits a very compact plant habit; reaching 40 cm in height as a four year-old plant in the landscape.
2. 'Hoogi021' exhibits leaves that emerge brown-purple and mature to green suffused with black.
3. 'Hoogi021' exhibits very small sized leaves.
4. 'Hoogi021' exhibits small white-pink flowers in spring.

'Monlo', the female parent of 'Hoogi021', differs from 'Hoogi021' in having a larger plant habit (reaching about 100 cm in height in four years in the landscape) and in having leaves that are larger and darker and less green in color. 'Hoogi021' can also be compared to the cultivar 'Donna May' (U.S. Plant Pat. No. 22,634) and and 'Hoogi018' (U.S. Plant patent application Ser. No. 14/756,843). 'Donna May' is similar to 'Hoogi021' in having a compact plant habit and small leaves, however 'Donna May' differs from 'Hoogi021' in having purple leaves throughout the growing season. 'Hoogi018' is similar to 'Hoogi021' in having a very compact plant habit and small leaves. 'Hoogi018' differs from 'Hoogi018' in having leaves that are grey-purple-red in color.

BRIEF DESCRIPTION OF THE DRAWINGS

The accompanying colored photographs illustrate the overall appearance and distinct characteristics of the new *Physocarpus*. The photographs were taken of a plant 18 months in age in age as grown outdoors in a 21-cm container in Ederveen, The Netherlands.

The photograph in FIG. 1 provides a side view of the plant habit of 'Hoogi021'.

Figure 1:
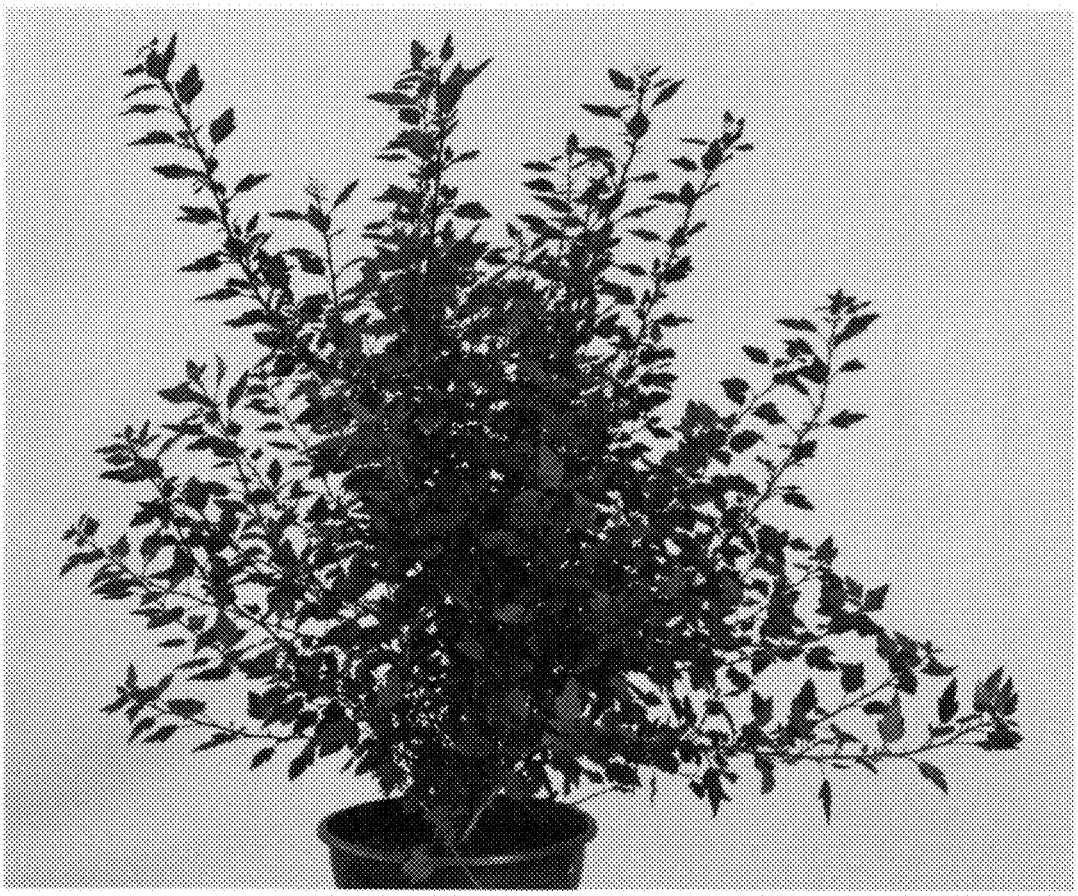
Figure 2:
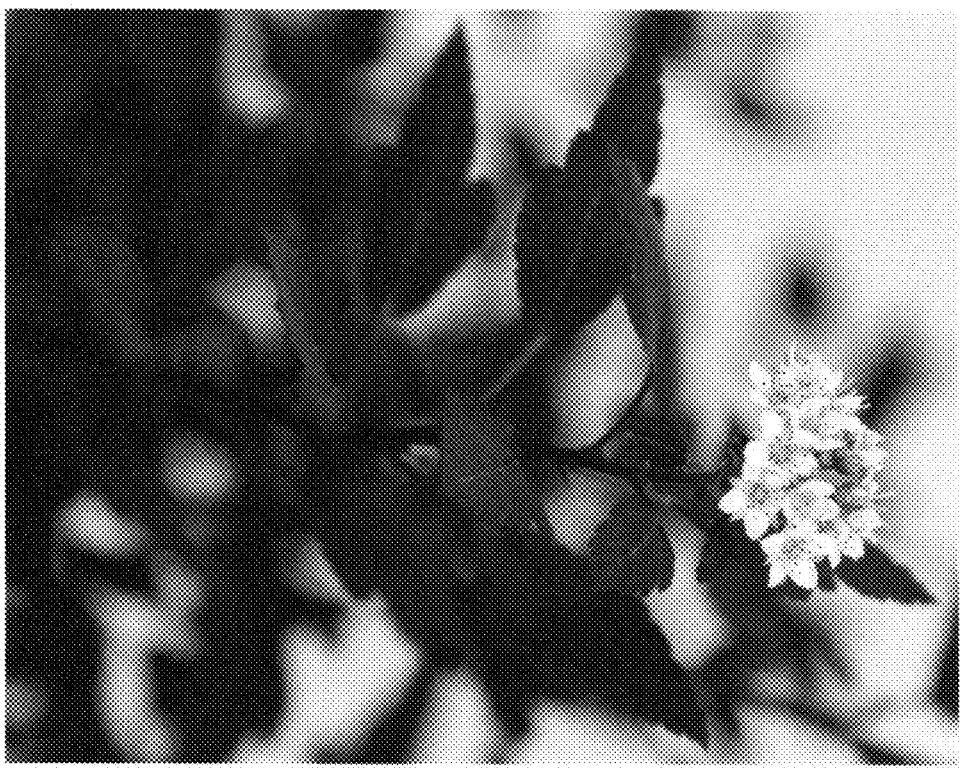

The photograph in FIG. 2 provides a close-up view of an Inflorescence of 'Hoogi021'.

Figure 3:
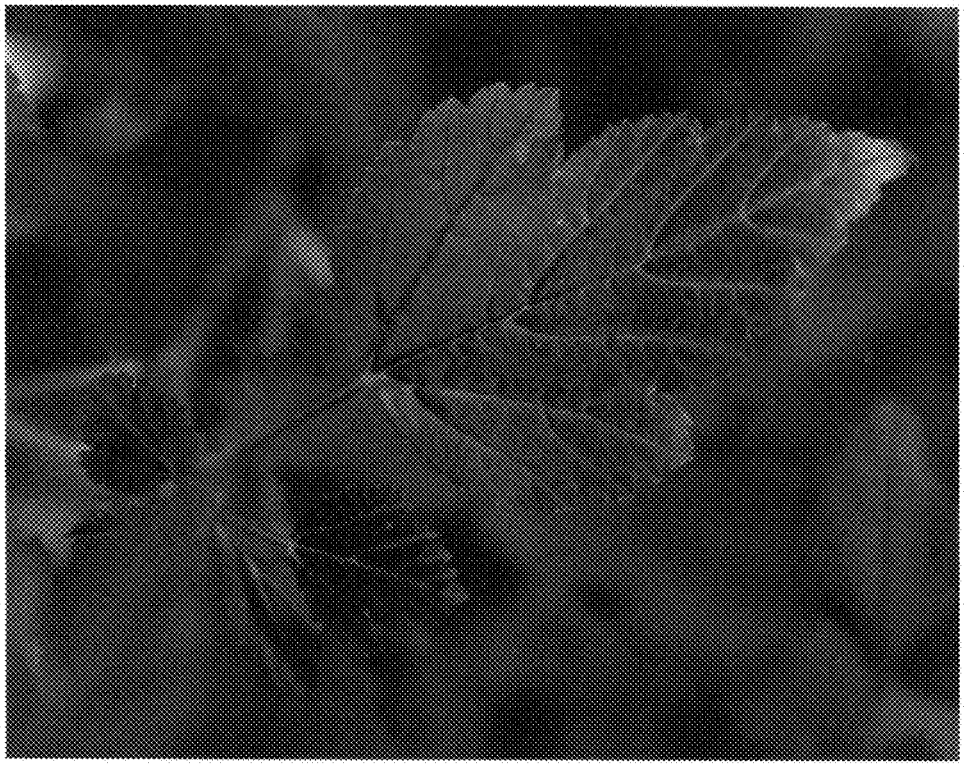

The photograph in FIG. 3 provides a close-up view of a leaf of 'Hoogi021'.

The colors in the photographs are as close as possible with the digital photography and printing techniques utilized and the color codes in the detailed botanical description accurately describe the colors of the new *Physocarpus.*

BOTANICAL DESCRIPTION OF THE PLANT

The following is a detailed description of 18 month-old plants of the new cultivar as grown outdoors in 21-cm containers in Ederveen, The Netherlands.mnPhenotypic differences may be observed with variations in environmental, climatic, and cultural conditions. The color determination is in accordance with The 2015 R.H.S. Colour Chart of The Royal Horticultural Society, London, England, except where general color terms of ordinary dictionary significance are used.

General description:

*Blooming period*.—About 3 weeks in early summer in The Netherlands.

*Plant type*.—Perennial shrub.

*Plant and growth habit*.—Very compact, mounded.

*Height and spread*.—An average of 61.5 cm in height and 73.3 cm in spread as grown in a 13 cm container.

*Cold hardiness*.—At least to U.S.D.A. Zone 3.

*Diseases and pest resistance*.—Similar susceptibility and resistance to diseases and pests to other *Physocarpus* cultivars.

*Root description*.—Fibrous and fine.

*Growth rate*.—Vigorous.

*Propagation*.—Softwood stem cuttings.

*Root development*.—An average of 4 weeks to produce a rooted cutting and about 12 months weeks to produce a fully rooted plant in a 12.5-cm container.

Branch description:

*Branch color*.—New wood; 183B, older bark; 199D with exfoliating bark a blend of 164A and 166A.

*Branch size*.—An average of 35.9 cm in length and 2 mm in diameter.

*Stem aspect*.—Lateral branches are held in an average angle of 70° to soil level (=0°), some branches vary between 50° and 90°.

*Number of lateral branches*.—An average of 87 per plant.

*Branch surface*.—Slightly glossy.

*Branch shape*.—Rounded and slightly angled.

*Branch internode length*.—An average 1.5 cm.

*Branch habit*.—Very freely branching, lateral branches emerge from the base and from the main stems.

*Branch strength*.—Strong.

Foliage description:

*Leaf shape*.—Ovate, tri-lobed.

*Leaf division*.—Simple.

*Leaf base*.—Truncate to obtuse.

*Leaf apex*.—Acute.

*Leaf venation*.—Pinnate, color; upper surface 152C, lower surface N148C.

*Leaf margin*.—Biserrate to bicrenate.

*Leaf attachment*.—Petiolate.

*Leaf arrangement*.—Alternate.

*Leaf surface*.—Both surfaces glabrous, upper surface moderately glossy and lower surface matte.

*Leaf size*.—An average of 3.3 cm in length and 2.4 cm in width.

*Leaf number*.—Average of 24 per lateral branch.

*Leaf color*.—Young foliage upper surface; 200A, very slightly tinged N186C, young lower surface; 148A, mature foliage upper surface; 147A, strongly tinged 202A, mature lower surface, 148B.

*Petiole*.—Flattened in shape, an average of 1.4 cm in length, 1 mm in width, color is 152D, tinged 178A, lower side N148B.

*Stipules*.—2 present at the base of each petiole, leafy, narrow oblong to oblanceolate in shape, acute tip, broadly cuneate base, an average of 4 mm in length and 5 mm in width, color; upper and lower surface 146B, base tinged 150D to 180B to 180C, dropped when leaves mature.

Flower description:

*Flower type*.—Small rotate flowers arranged in spherical corymbs.

*Flower fragrance*.—None.

*Flower lastingness*.—Average of one week.

*Flower bud description*.—Ovate in shape, average of 3 mm in length and 2 mm in diameter, color; 65B to 65D, immature sepals are 144B, margined 60D.

*Flower quantity*.—Average of 12 flowers per lateral stem.

*Inflorescence size*.—Average of 1.6 cm in height and 2.1 cm in width.

*Flower size*.—About 5.5 mm in depth, 4.5 mm in diameter.

*Peduncles*.—About 5 mm in length and 0.75 mm in diameter, 152D in color, glabrous surface, moderately strong in strength, held straight on top of lateral branches (=0°).

*Pedicels*.—About 7 mm in length and 0.5 mm in diameter, 152D in color, glabrous surface, moderately strong in strength, held in an average of 70° to peduncle (=0°), varying between 50° and 90°.

*Petal description*.—5, upright, rotate, ovate in shape, margin is entire, apex is acute, lower and upper surface are matte and glabrous, base is rounded.

*Petal size*.—Average of 2.2 mm in length and 1.5 mm in width.

*Petal color*.—Opening; upper surface 69D, lower surface 68D to 69A, fully open; upper surface; between 69D and N155B, lower surface; between 69A to 69B, fading to N155B.

*Calyx size*.—Rotate and slightly cup-shaped, average of 2.5 mm in length and 5.5 mm in diameter.

*Sepal description*.—5, narrow ovate in shape, margin is entire, apex is narrowly acute, surface is glabrous and matte, an average of 2 mm in length and 1.2 mm in width, color of immature upper surface; between 150C and 150D, color of immature lower surface; 144B, margined 60D, color of mature upper surface; 150C to 150D, color of mature lower surface; 144B, margined 60D.

Reproductive organs:

*Gynoecium*.—Pistil; average of 4, average of 2.5 mm in length, stigma; club-shaped, 151B in color, style; average of 2.3 mm in length, 150B in color, ovary is 144C in color.

*Androecium*.—Stamens; average of 25, anthers; globular in shape, average of 0.2 mm in length and 200A to 202A in color, no pollen detected.

*Fruit and seed*.—No fruit or seed detected.

It is claimed:

1. A new and distinct cultivar of *Physocarpus* plant named 'Hoogi021' substantially as herein illustrated and described.

* * * * *